(12) United States Patent
Voinov

(10) Patent No.: US 6,629,993 B2
(45) Date of Patent: Oct. 7, 2003

(54) FLEXIBLE EXPANDABLE SHEET STENT AND TECHNOLOGY OF ITS MANUFACTURING

(75) Inventor: Valarian Voinov, Jerusalem (IL)

(73) Assignee: Brainwave Cardiovascular Technologies, Ltd., Jerusalem (IL)

( * ) Notice: Subject to any disclaimer, the term of this patent is extended or adjusted under 35 U.S.C. 154(b) by 0 days.

(21) Appl. No.: 09/825,639

(22) Filed: Apr. 4, 2001

(65) Prior Publication Data

US 2002/0002398 A1 Jan. 3, 2002

Related U.S. Application Data

(63) Continuation of application No. PCT/IL98/00484, filed on Oct. 4, 1998.

(51) Int. Cl.⁷ .................................................. A61F 2/06
(52) U.S. Cl. ..................................................... 623/1.15
(58) Field of Search ...................... 623/1.15, 1.11–1.18, 623/1.2–1.23, 1.5–1.53; 606/194, 195, 191

(56) References Cited

U.S. PATENT DOCUMENTS

| | | | |
|---|---|---|---|
| 5,133,732 A | * | 7/1992 | Wiktor ....................... 623/1.15 |
| 5,554,181 A | | 9/1996 | Das |
| 5,591,230 A | * | 1/1997 | Horn et al. ................. 623/1.15 |
| 5,618,301 A | | 4/1997 | Hauenstein et al. |
| 5,824,056 A | * | 10/1998 | Rosenberg ................. 623/1.15 |
| 5,855,597 A | | 1/1999 | Jayaraman |
| 5,868,783 A | | 2/1999 | Tower |
| 5,931,866 A | * | 8/1999 | Frantzen .................... 623/1.15 |
| 6,187,034 B1 | * | 2/2001 | Frantzen .................... 623/1.15 |
| 6,187,036 B1 | * | 2/2001 | Shaolian et al. ........... 623/1.15 |

\* cited by examiner

Primary Examiner—Michael J. Milano
Assistant Examiner—(Jackie) Tan-Uyen T. Ho
(74) Attorney, Agent, or Firm—Reed Smith LLP; William H. Dippert

(57) ABSTRACT

A flexible expandable sheet stent is intended for the better support of a diseased vessel wall on the basis of securing the very best characteristics and raising the serviceability of a stent in a vessel. The stent comprises constructive elements, preliminarily formed in the shape of a stencil on the thin sheet metallic blank surface. The stent's constructive elements include a saw-shaped profile made of teeth from which the relatively rigid band in the shape of consecutively-united pockets is formed. In a passage formed of consecutively-united pockets, a polymer thread with a fixed length loaded with medical preparations for local drug delivery is deployed. The implantation of the stent in a vessel under X-ray is performed in such a way as to locate the relatively rigid band of consecutively-united pockets on the side of the vessel wall adjoining the cardiac muscle.

11 Claims, 10 Drawing Sheets

FLEXIBLE EXPANDABLE SHEET STENT AND TECHNOLOGY OF ITS MANUFACTURING

This application is a continuation of co-pending PCT Patent Application No. PCT/IL98/00484, filed Oct. 4, 1998, the entirety of which is incorporated herein by reference.

FIELD AND BACKGROUND OF THE INVENTION

The present invention relates generally to medical technology, particularly to expandable cardiovascular stents, which are intended for radical arterial lumen recovery with subsequent restoration of normal blood flow. In the present application the term "stent" refers to a device designed to expand a blood vessel and to maintain the achieved size of a lumen. Traditionally stents are delivered to a target area in the cardiovascular system on an inflatable balloon located on the tip of a transluminal catheter. Then, the balloon is inflated, leading to the expansion of the stent thereby widening the lumen of the vessel. Other less common systems for stent delivery also exist.

BACKGROUND OF THE INVENTION

Most of the existent stents are made from metal. Examples of common designs are set forth in, for example, U.S. Pat. Nos. 4,733,665, 4,969,458, 5,102,417, 5,195,994, 5,513,444, and PCT International Publication No. WO 91/013820, all of which are incorporated herein by reference. Certain properties of any metallic surface lead to thrombogenicity of a stent once it is implanted within the human cardiovascular system. Therefore, one of the important directions in stent development is the improvement of stent thromboresistance because this would reduce the systemic anticoagulation therapy, thereby reducing the complication rate after stent implantation. At present none of the metallic stent designs have achieved the delicate balance between desired durability to sufficiently support the vessel wall and flexibility to reduce the thrombogenicity and intimal hyperplasia. Thus, there is a substantial need for anticoagulation and thrombolitic therapy following stent implantation.

The use of metal in stent design has additional drawbacks. One of the limitations of metallic stents is the presence of a more or less rigid kinematic link between constructive elements of radial strength and flexibility. This factor creates additional difficulties during the delivery of the stent to a target area in the coronary artery, especially in distal segments of the vessel. This factor also plays a major role in the shortening of the stent upon stent expansion, which may lead to the sub optimal implantation of the stent, especially in diseased segments of blood vessels, and also this may activate undesirable post-procedural processes, such as thrombosis and restenosis.

The rigidity of a kinematic link between the constructive elements of radial strength and flexibility in already complicated geometrical forms of the stent structure does not permit the use of thin metal plates in stent manufacture. On the contrary, it requires high inflation pressures upon the deployment of a stent to prevent the stent from collapsing into the vessel lumen. However, ideally a stent structure should combine longitudinal flexibility and radial rigidity, which would correspond optimally to the characteristics of pulsating coronary arteries.

Despite the fact that the descriptions of most conventional stents claim that they are low profile stents, in fact, all known stents have profiles in the range of from about 1.3 to 1.6 mm. This is due to the limitations of the technology of stent manufacture. All stents are placed on balloons with a minimal diameter of 1.6 mm, which already restricts clinical application of stents in small vessels. There is no known stent having parameters that would permit it to be used in vessels of 2 mm or less. Another advantage of stent structure is an ability to perform an adjunctive angioplasty after the deployment of the stent. This also permits the better adjustment of the stent to the arterial wall due to the deeper penetration of the stent outer elements into the media and the atherosclerotic plaque. A disadvantage, on the other hand, is the metallic surface of a stent in general, and especially the texture of the surface, which can attract blood elements and activate the formation of thrombus, as well as initiate an exaggerated healing process, i.e., the proliferation of smooth muscle cells that can result in restenosis.

Therefore, an important part of stent design is the ability to incorporate various bioabsorbable polymers, which can be loaded with antithrombotic and/or antiproliferative pharmacologic agents in high concentrations. These agents, delivered locally into the arterial wall, can prevent thrombosis and neointimal proliferation and also avoid unwanted systemic side effects. However, so far the results of clinical experiments with polymer coated stents show frequent occurrence of inflammatory reactions to the polymers by the vessel wall, which limits their clinical application. Another important limitation of stent use is the expensive technology required for stent manufacture, which involves laser technology in almost all known stents. This lowers the cost-effectiveness of the device and, therefore, its utilization in clinical practice. This technology also leaves the quality of a stent's surface suboptimal, with subsequent higher percentage of thrombus formation on this surface. The "ideal" stent should possess the following high quality properties: flexibility, trackability, non-shortness, ultra-low profile, visibility in X-rays, thromboresistance, biocompatibility, reliable expandability, wide range of available sizes, optional capability of the local drug delivery, and low cost (see, P. Ruygrokand P. Serruys Intracoronary stenting. "Circulation", 1996, 882–890). These features will widen clinical applications of stenting, enable the reduction of unwanted side effects, and ultimately improve the clinical outcome.

An effective technical stent design executed from slotted tubes simultaneously combines flexibility and sufficient radial strength, as is shown, for example, in PCT International Publication No. WO 98/20927, incorporated herein by reference. A more progressive stent design is disclosed in the PCT patent application No. PCT/IL 98/00189, filed Apr. 21, 1998, incorporated herein by reference. In this prototype design (FIGS. 1, 2) the constructive elements, preliminary shaped as a stencil on a thin sheet metallic blank surface, form flexible twisting loops (1), closed on two bands (2) and (3) as consecutively united pockets. Before the installation of the stent, branches of loops (1) are in turn oppositely moved apart in such a way that each pair of loops is transformed into a shape close to that of a circle (ring). Then, after the calibration, the stent is located on an inflatable balloon (4) of a delivery catheter for its subsequent introduction into an afflicted vessel. However, this known stent has a substantial disadvantage: the presence of a critical plane on which the appositively located bands (2,3) in a shape of the consecutively united pockets are located. This plane has proven to be very rigid and, upon the deformation for bending, can hamper overcoming a vessel's anatomic curvature. This characteristic hinders location of this known stent in curved vessels as well as creation of stents of a required length. In practice several stents have to be implanted in a row, which prolongs the time of intravascular intervention and causes additional vessel trauma.

In other axial planes at the known stent bending rigidity is minimized in the plane perpendicular to a critical one. However, in all cases, excluding the last one, the bands (2, 3) with the chains of the united pockets change their length due to the bending deformation. The band length increases on the outward radius and decreases on the inward one upon the bending of a stent in a vessel. This prohibits accurately determining the length of a polymer thread loaded with medicinal preparations for local drug delivery. The thread's length should not be less than that of an extent of the united pocket chain on the stent bending outward radius, corresponding to its maximal tension. This could lead to the sag of the polymer loaded thread on the stent bending inward radius and to the jamming of it among the loops (1).

A shift from the critical plane in such a stent design could be partially done by twisting the bands (2,3) in relation to the longitudinal axis in such a way that the chain bands of consecutively united pockets locate in the spirals. However, it does not fully solve the rigidity problems, and, in addition, the twisting (and a possible untwisting) of the stent leads to the changing of its axial and radial sizes, as well as to the changing in the distance among loops (1). The restriction of the vessel wall natural movements could promote the development of stenosis. An attempt to prevent the vascular stenosis with a help of a stent will be more successful the more flexible the stent and the less it restricts the possible natural local vessel wall movements. The presence in a prototype-stent of the two comparatively rigid bands (2,3) with consecutively united pockets chains upon the close contact with a vessel wall greatly limits the degrees of freedom of its wall. This may become the cause for restenosis. The practical work shows that after the installation of the sufficiently rigid stent in a vessel of a developed length, restenosis occurs in more than 25% of the clinical cases.

SUMMARY OF THE INVENTION

According to the invention a stent has increased flexibility with a container for a polymer loaded thread of a fixed length, whereas there is support for the favorable dynamic action on a vessel wall (of a massage type). Also, the consequences of edge effects from blood flow action on the stent face end surface sections in a vessel are avoided. Further, a stent configuration has diameters differentiated in length for a simultaneous deployment in a main vessel and in one of its bifurcations with an increased rigidity for a better fixation of the stent in the place of vessel diameters transition. This is achieved by the fact that in a flexible expandable sheet stent design constructive elements, preliminarily formed as a stencil on a thin sheet metallic blank surface, in their regular form represent one relatively rigid band consisting of consecutively united pockets, the branches of which form periodically repeating winding closed outlines, whereas the components of the longest sides of each outline are oppositively located in a form of a closed free loop with a configuration that approximates a circle, forming an independent ring with a fastening point on the relatively rigid band. In the preliminarily formed stencil, the stent constructive elements occupy the primary part of the area of the sheet, excluding that which falls at the stencil slots, at the radii of the formed pockets rounding off and the radii of free loops short closed sides. The width of the slots is executed as minimally possible technologically.

According to the invention the pockets of the stent are formed by the bending of a saw-shaped profile that is a component of the closed free loops foundation, whereas the bending of the pockets is executed into one or alternatively into different sides for an angle of the order of 120°. The polymer loaded thread of a fixed length is placed in the consecutively united pockets.

In the stent of the invention the short sides of the closed free loops on the stent end side surfaces are fastened by the fragments of the relatively rigid band in a shape of the pockets, whereas in case of stent diameter differentiated in its length according to the different diameters and extent of the afflicted vessel by the said fragments of the relatively rigid band in a shape of the pockets are fastened the short sides of the closed free loops in the place of their transition from one stent diameter to the other. Single closed free loops are uniformly distributed along the stent length or in places, where the increased flexibility is most desirable, including a construction variant with one closed free loop, placed in the stent middle part, whereas the other short sides of the loops are executed in a shape of a relatively rigid band consisting of the consecutively united pockets.

The technological manufacturing process of the proposed stent design includes the following steps:

separation of the thin sheet metallic blank with a multiple unwasted quantity of the stent designs;

execution of a calculated geometrical profile stencil of stent constructive elements on the surface of the thin sheet metallic blank;

shaping of consecutively united pockets by bending;

deployment of the stencil into a step-by-step gauge fixing the distances among the closed free loops;

introduction of cylindrical gauges into all said loops, positioning appositively the long sides of the each loop and trying to achieve the stent minimal diameter necessary for an uninflated balloon;

fixation of the stent on an uninflated balloon of a delivery catheter;

positioning and fixation of a polymer loaded thread in a passage formed by the chain of the said consecutively united pockets; and packing of a ready device.

In the case of using a variant of the stent design with single free loops, uniformly distributed along the stent length or in the places where the increased flexibility is most desirable, the technological process includes the set of prototype stent steps exclusively.

Implantation of the stent in a blood vessel, preferably controlled by use of X-ray, is executed in such a way as to provide the location of the relatively rigid band of the consecutively united pockets on a vessel wall adjoining the cardiac muscle. As a result, the stent, with one relatively rigid band of the consecutively united pockets, preserves all the positive properties of the prototype stent while possessing an increased flexibility, making it possible to carry out successively the complex intravascular angioplasty and, if necessary, to install stents of enlarged length. The maximal flexible rigidity of the stent is at least half or less as the minimal rigidity of the prototype stent. Since the band with consecutively united pockets (a container for the polymer loaded thread) can bend in all the spatial directions but does not share in the stent bending, determined by its cross-sections, then the size of the axial band, and consequently of the polymer loaded thread, remains invariable. In case of the band with the consecutively united pockets adjoining the cardiac muscle, the flexibility of this band in the direction of the cardiac muscle functioning is minimal. Therefore, any pulsation of the cardiac muscle (dynamic action) is taken by the band effectively enough.

The dynamic actions from this band are transmitted to the loops, independently to some extent, and the loops, resting against the opposite vessel wall, exert a massaging action on it, without practically limiting the pulsating vessel degrees of freedom.

The stent can have a partially increased rigidity at any place of its linear length at the expense of fastening the loop short sides by the fragments of the relatively rigid band in the shape of the pockets. For example, by fastening in this way the stent end loops, the rigidity of end surface sections increases, and the possibility of their deformation from the blood flow action decreases. By fastening the joining loops of the stent, differentiated in diameter, the rigidity of the design middle part increases, thus increasing the fixation reliability of a stent part with a greater diameter, preventing its penetration into a vessel with a lesser diameter.

At the same time the relatively increased stent rigidity in a transitional section of a vessel promotes a more efficient destruction of the pathological formations in the place of implantation.

The stent sections with fragments, increasing its rigidity, resemble the prototype stent design. Since the relative rise in stent rigidity takes place on the longitudinal extent of small length fragments only, then the general design flexibility does not decrease and remains as intended.

It is possible to fragmentarily insert into the stent not only the increased rigidity but also an increased flexibility with the help of separate single free loops arranged in the stent along the stent's length. The increased stent flexibility takes place in the zones of separate single free loops location.

BRIEF DESCRIPTION OF THE DRAWINGS

This invention is herein described with the use of examples and references to the accompanying drawings, wherein.

DETAILED DESCRIPTION OF THE INVENTION

Figure 1:
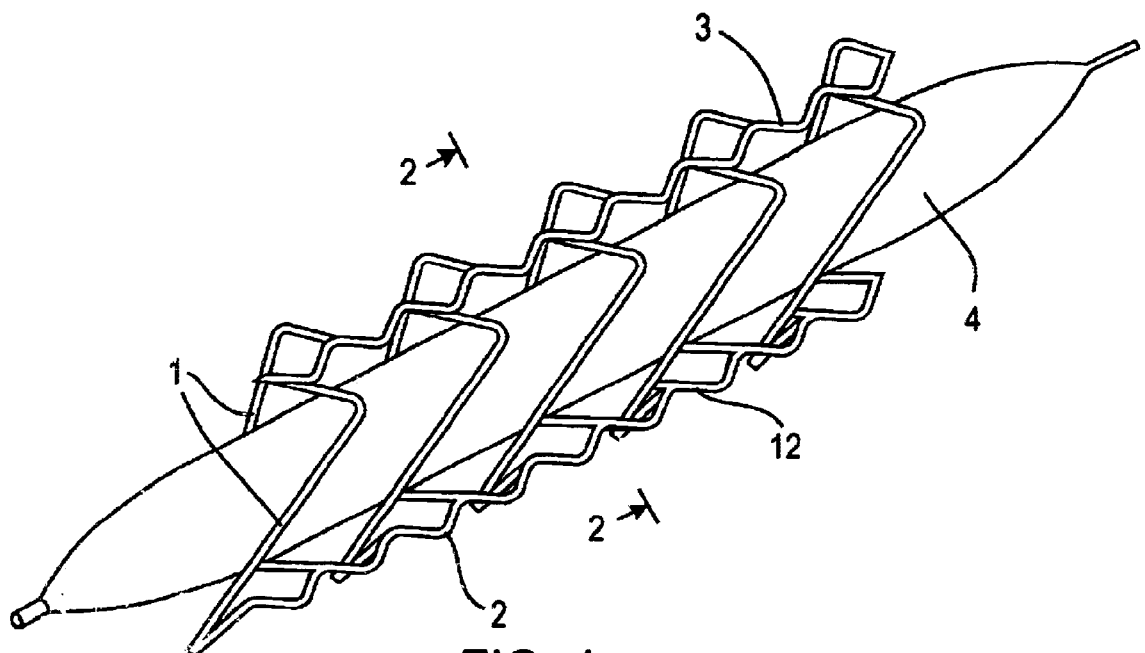
FIG. 1 shows a stent of the prior art located on an uninflated balloon of a delivery catheter.
Figure 2:
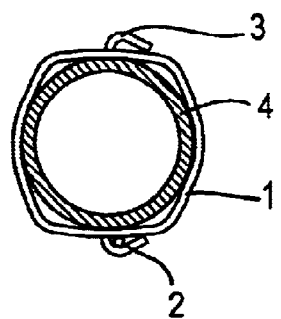
FIG. 2 shows a cross-sectional view of the stent shown in FIG. 1 across line A—A.
Figure 3:
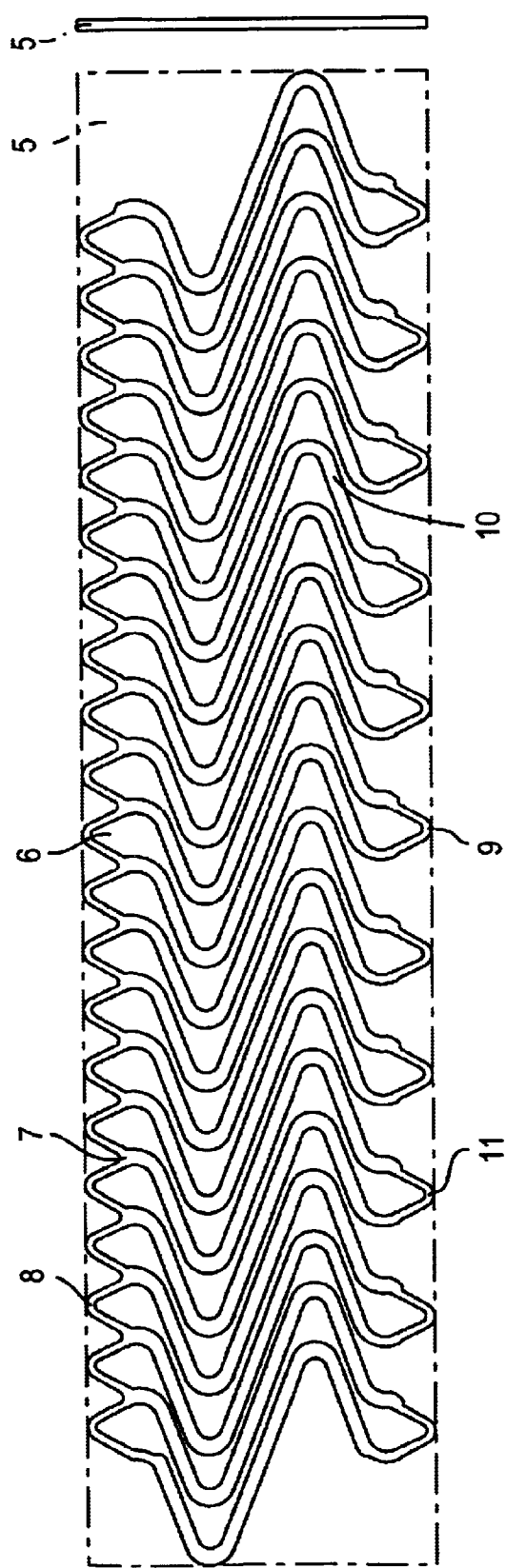
FIG. 3 shows a stent constructive element stencil executed on a thin sheet metallic blank surface, according to the invention.

The invention can perhaps be better appreciated by making reference to the drawings. In FIG. 3 a stencil with stent pre-determined geometrical sizes is formed on a thin sheet metallic blank (5). At the same time slots (6) forming constructive elements (7) of a future stent are also shown: the free loop long sides, the saw-shaped profile, the free loop short sides and the necessary radii of the rounded units. The constructive elements (7) consist of four parts: A saw-shaped profile tooth (8) from which a pocket will be formed. For forming a pocket the saw-shaped tooth (8) is bent for an angle of the order of about 120°. A chain of consecutively united pockets forms a relatively rigid band along the future stent longitudinal axis. The two other parts are free loops twisting long sides (9) and (10). The short side of the twisting closed outline in the stencil constructive elements is generally designated as (11).

Figure 4:
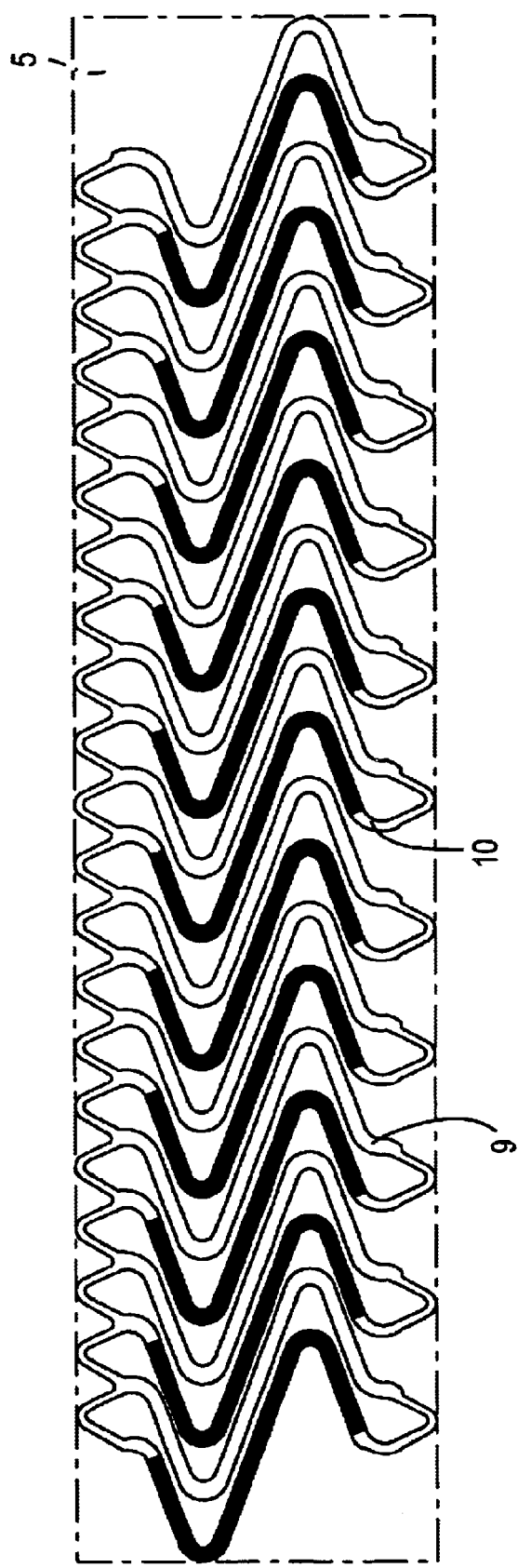
FIG. 4 shows the same as on FIG. 3, but with one of the opposite free branches being blackened (for example, the blackened loop branch will be located under the balloon, whereas the unblackened one will be located over it)
Figure 5:
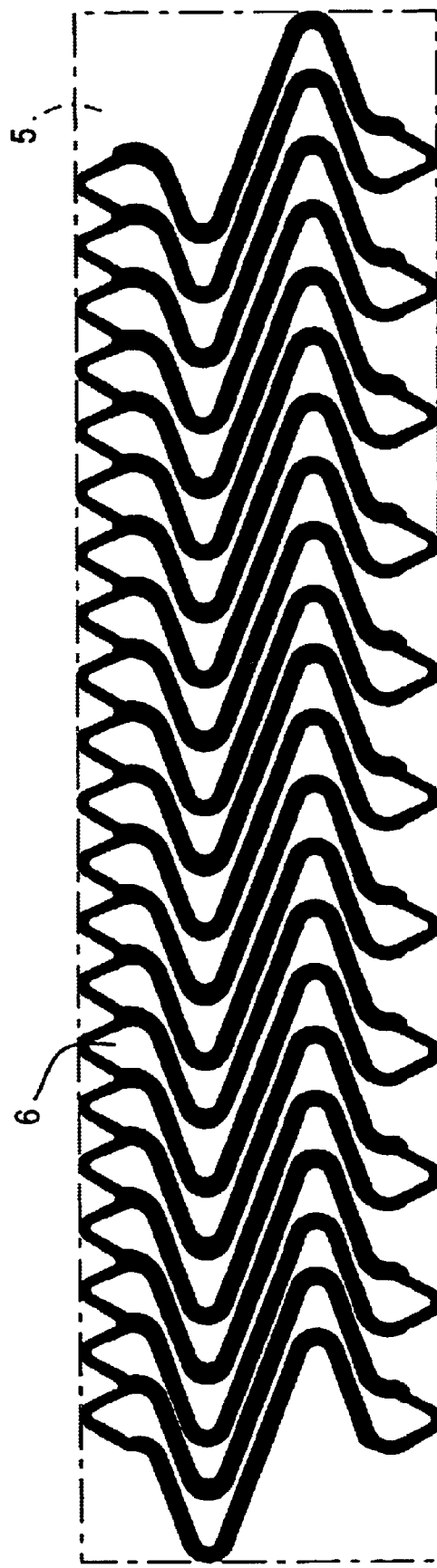
FIG. 5 shows the same as on FIG. 3, but with the blackened stencil constructive elements and with unblackened slots.

Thus, every closed loop is based on the pocket branches. FIG. 4 shows stent constructive elements formed on the thin sheet metallic blank surface with one of the outline twisting closed sides (9) blackened and with the other outline closed side (10) left clear. This figure helps to explain how in the future stent volumetric cylindrical design with closed rings is formed from the thin sheet metallic blank (5). For example, an uninflated balloon (not shown here) is threaded through the design elements in such a way that every blackened free loop branch (9) is placed under the balloon whereas every unblackened free loop branch (10) is placed over the balloon. The stencil relative sizes do not allow it to be depicted graphically, and therefore FIG. 5 shows schematically for how much the unblackened slot (6) width is less than that of the future stent design elements (blackened).

Figure 6:
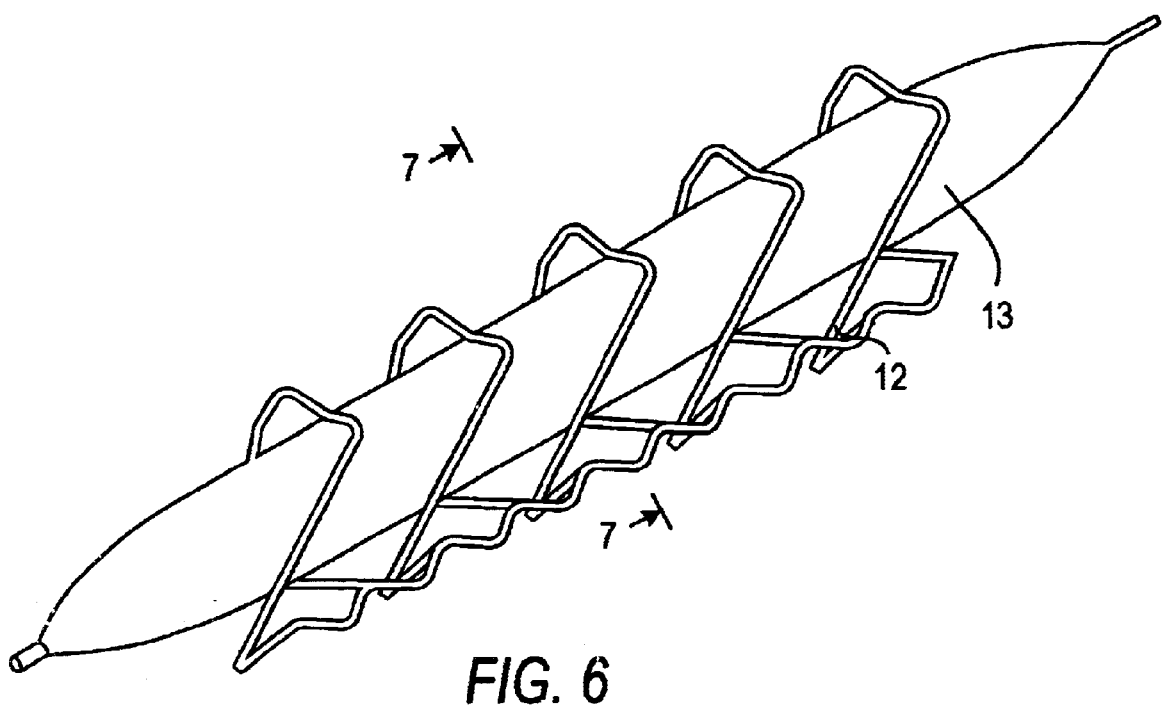
FIG. 6 shows another embodiment of the invention before expansion, located on an uninflated balloon of a delivery catheter.
Figure 7:
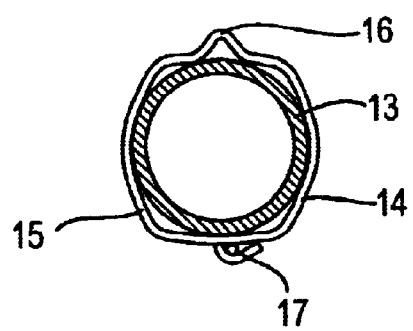
FIG. 7 shows a cross-sectional view of the embodiment shown in FIG. 6 across line B—B.
Figure 8:
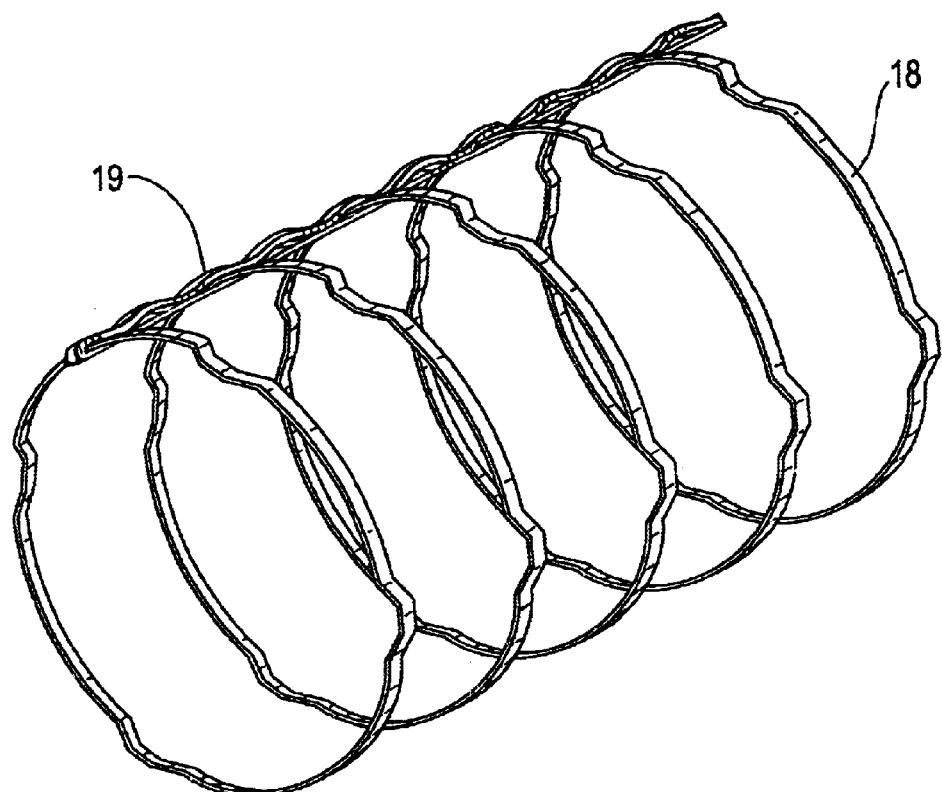
FIG. 8 shows a stent after expansion, according to the invention.
Figure 9:
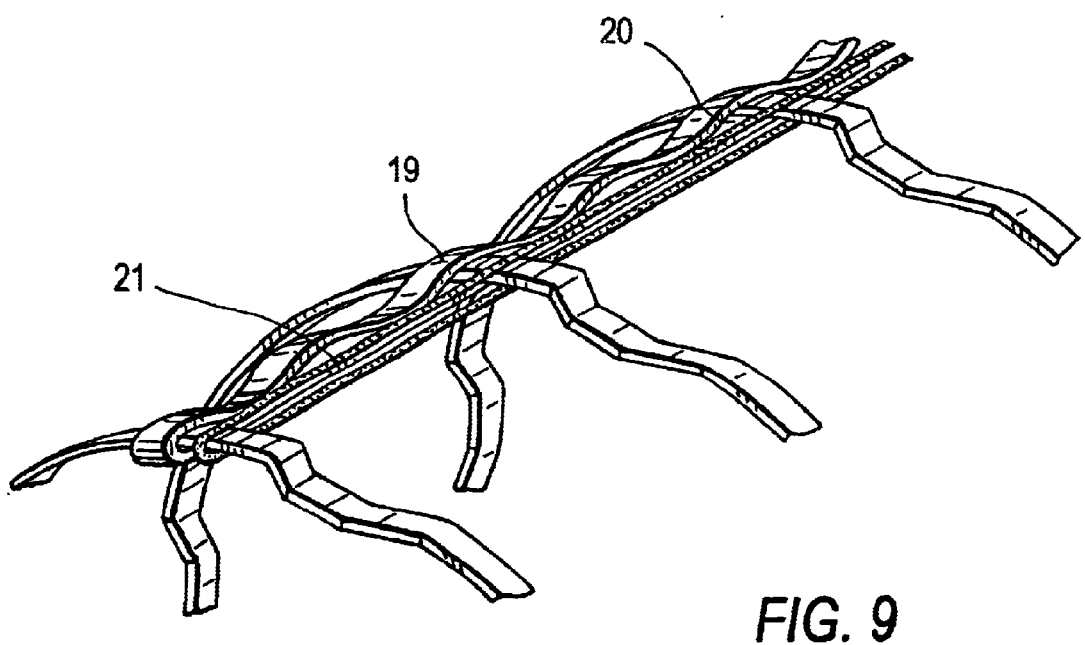
FIG. 9 is a partial, fragmented view of FIG. 8 in a place of polymer-loaded thread fixation in a last pocket of the relatively rigid band with the consecutively united pockets.
Figure 10A:
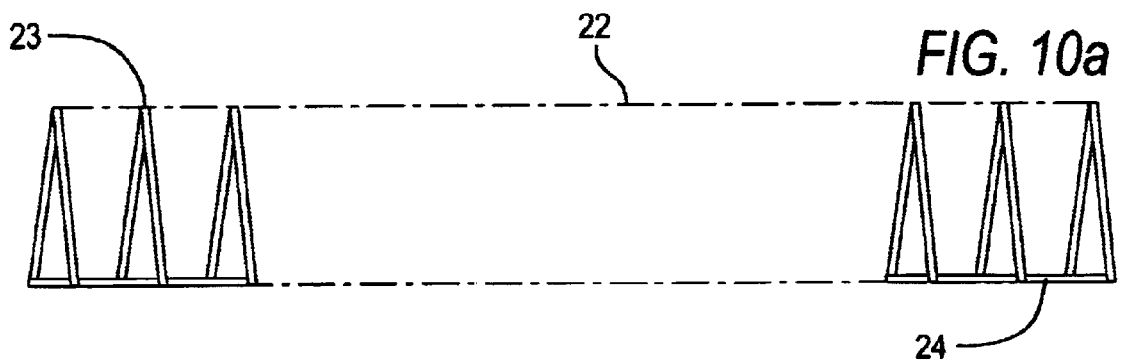
FIG. 10a is a schematic representation of a stent with a zero bend for the minimal rigidity plane, according to the invention.
Figure 10B:
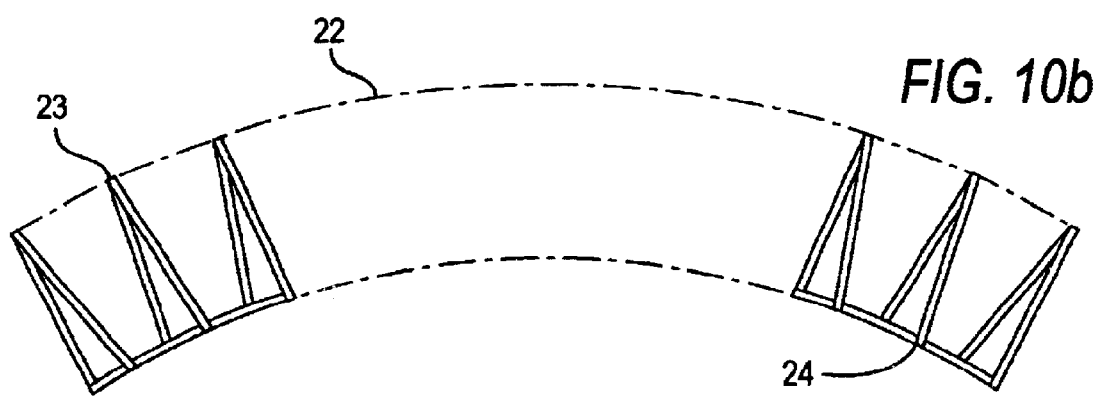
FIG. 10b is a schematic representation of a stent with a bend into the positive direction for the minimal rigidity plane, according to the invention.
Figure 10C:
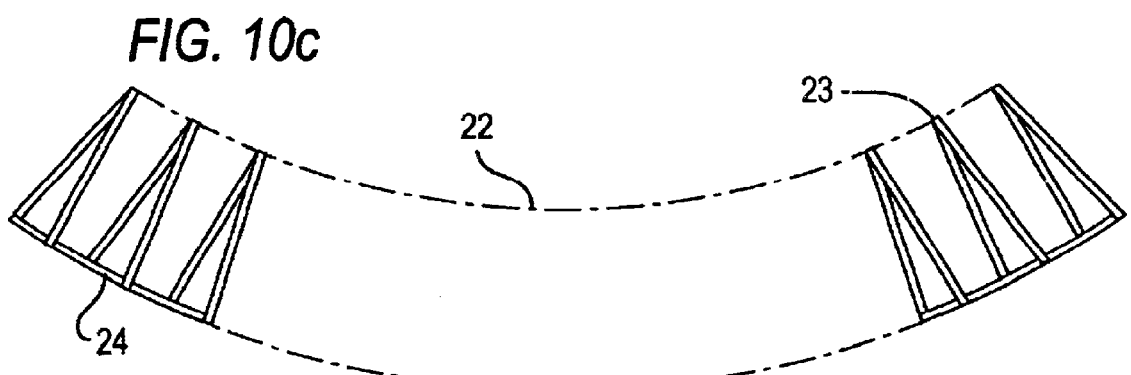
FIG. 10c is a schematic representation of a stent with a bend into the negative direction for the minimal rigidity plane, according to the invention.
Figure 10D:
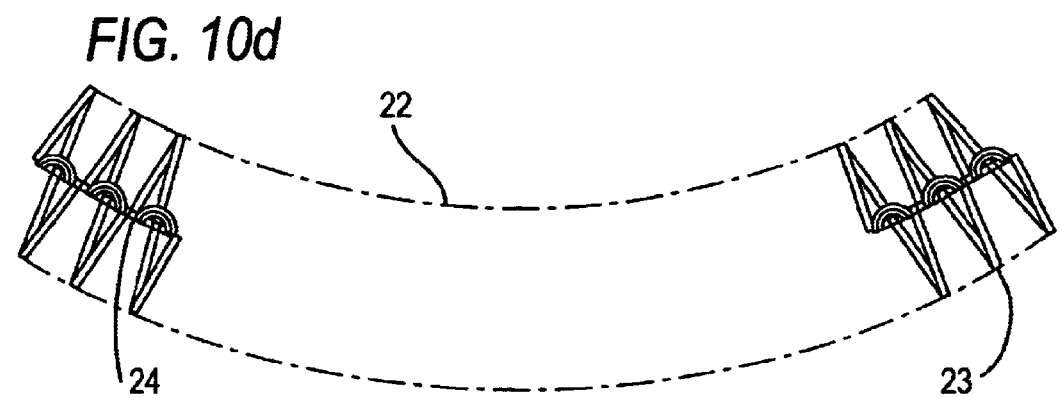
FIG. 10d is a schematic representation of a stent bend in its maximal rigidity plane, according to the invention.

FIG. 6 is a schematic representation of a stent (12) before expansion, located on an uninflated inflatable balloon (13) of a delivery catheter, whereas the balloon (13) is in fluid communication with an inflator (not shown). FIG. 7 is a cross-sectional view across line B—B in FIG. 6. Positions (14) and (15) denote the closed ring elements formed from the long twisting sides (9,10) of free loops. Position (16) denotes the closed ring elements formed from the free loop short side (11), while position (17) shows a pocket formed by the bending of tooth (8) (see FIG. 3). FIG. 8 shows a stent in an expanded state where closed loops are seen, i.e., rings (18) fastened to the relatively rigid band (19) formed by the chain of the consecutively united pockets (20). The fixation of a polymer thread (21) loaded with medicinal preparations for local drug delivery is seen here (FIGS. 5,8, 9).

The installation of a stent in a vessel is performed according to the generally known balloon expandable stent method after the fixation on a partially inflated inflatable balloon and delivery to the situs of a vessel pathological formation. Due to the control of the intravascular procedure in the X-ray, the stent is turned around the axis to make the rigid band from the chain of the consecutively united pockets face the cardiac muscle. The expansion of the stent is done by the inflation of the balloon over the limits of a plastic deformation to press the stent against the vessel wall, i.e., fixation on the vessel wall. At the conclusion of the procedure the balloon is deflated and withdrawn proximally, preferably through a catheter.

FIGS. 10a, 10b, 10c, and 10d are schematic diagrams of possible locations of stent (22) in a vessel with the different bending variants. The profiles of a closed ring (23) and of a relatively rigid band (24) with a chain of consecutively united pockets are marked on the diagrams. It is easy to imagine that if the band (24) is lying on the cardiac muscle, then the closed ring (23) does not limit the degrees of freedom of the vessel wall natural movements. In accordance with the executed stent design of 20 mm length 44 closed rings (23) are located on a band (24) from the chain of the consecutively united pockets. Such a frequency of ring deployment excludes the possibility of their "folding" (the loss of a radial size) under any actions from the pulsating vessel or cardiac muscle.

Figure 11:
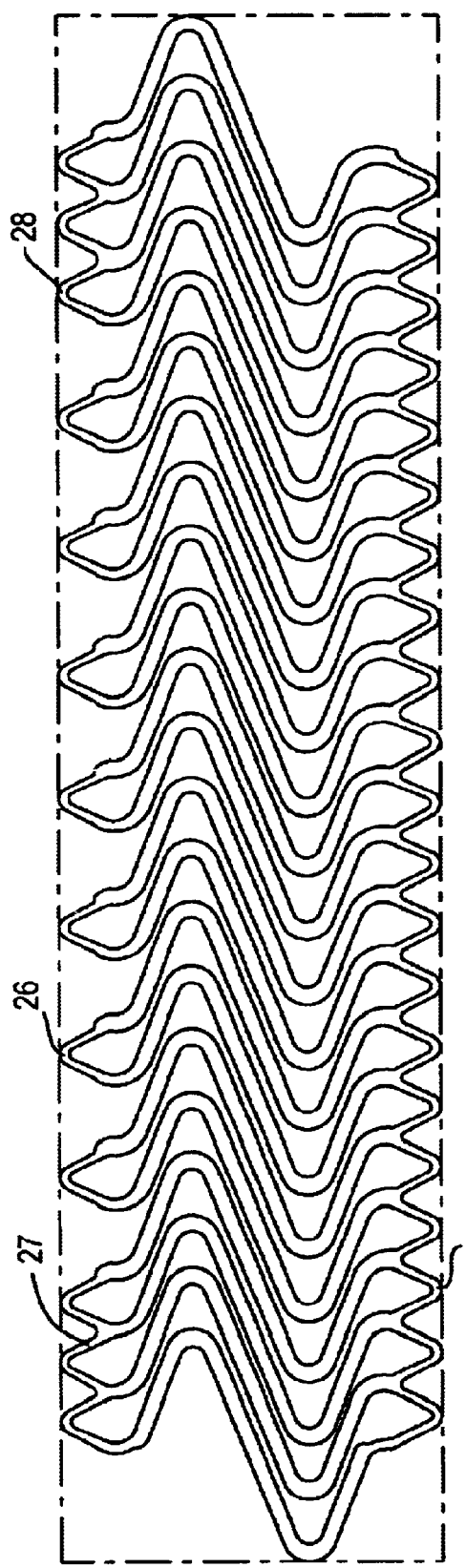
FIG. 11 shows a stent constructive element stencil with the fragments of the relatively rigid bands in a shape of blanks for the pockets located on the design end surface sections, according to the invention.

FIG. 11 shows a constructive elements stencil of the same stent as in FIG. 3 with a saw-shaped profile (25) and closed loops (26). However, there are some distinctions here: the fragments of the saw-shaped profile (27) and (28) are introduced on the future stent end surface sections for the relatively increased rigidity. The edges of section (27) and partially (25) as well as of section (28) and partially (25) in their design resemble a prototype stent.

Figure 12:
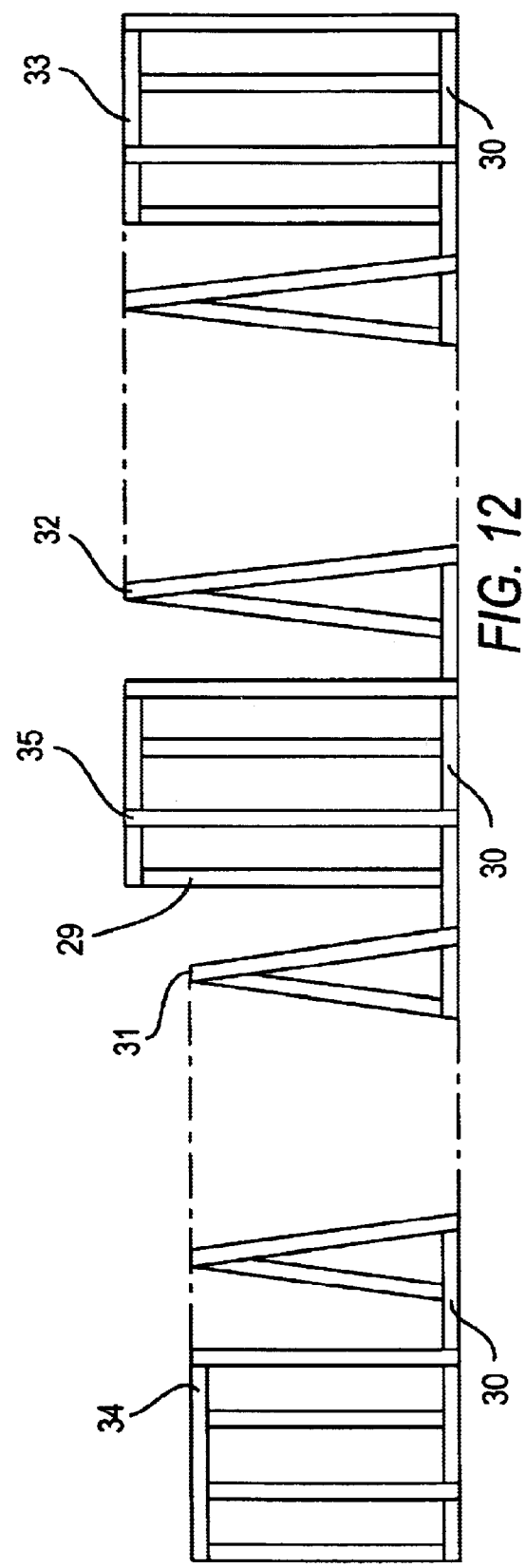
FIG. 12 is a schematic representation of a stent, differentiated as to the diameter length, with the fragments of the relatively rigid bands in a shape of the pockets located on the end surface sections of the design and in the place of diameter transition.

FIG. 12 is a schematic representation of a stent (29) differentiated with respect to the diameter length, consisting of a relatively rigid band (30) in a form of a chain of consecutively united pockets and closed loops of lesser (31) and greater (32) diameters. The fragments from the relatively rigid bands (33) and (34), consisting of pockets, secure the relative heightening of the rigidity on the stent end surface sections, whereas the band (35) relatively increases the stent (29) rigidity in place of transition from the greater (32) to the lesser (31) diameter.

Figure 13:
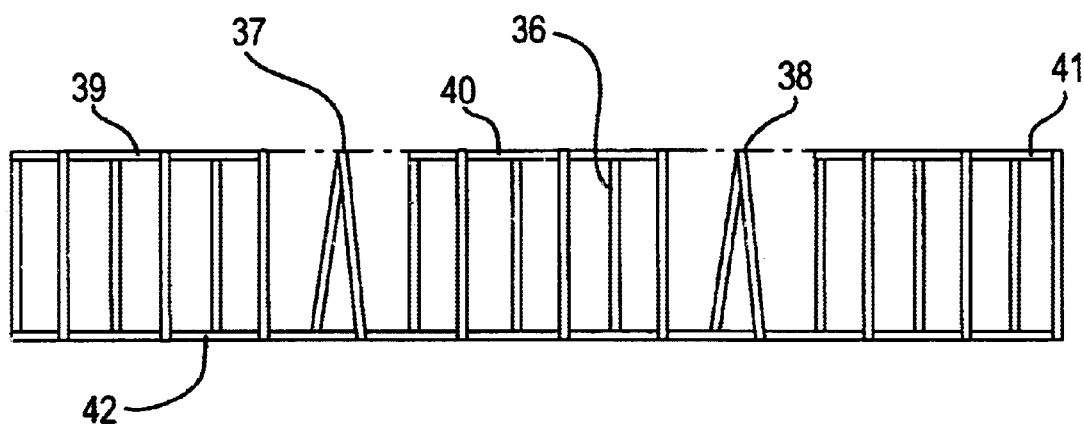
FIG. 13 is a schematic representation of a stent with separate free loops distributed uniformly along the stent length, according to the invention.

FIG. 13 is a schematic representation of a stent (36) with two single free loops (37) and (38) distributed uniformly along the stent length. These free loops (37, 38) divide the stent into three relatively rigid parts, fastened by the bands (39, 40, 41) and consisting of the consecutively united pockets. As in the main design (see FIGS. 3, 4, 5,10) the whole stent is united by a relatively rigid band (42) a chain of the consecutively united pockets.

Figure 14:
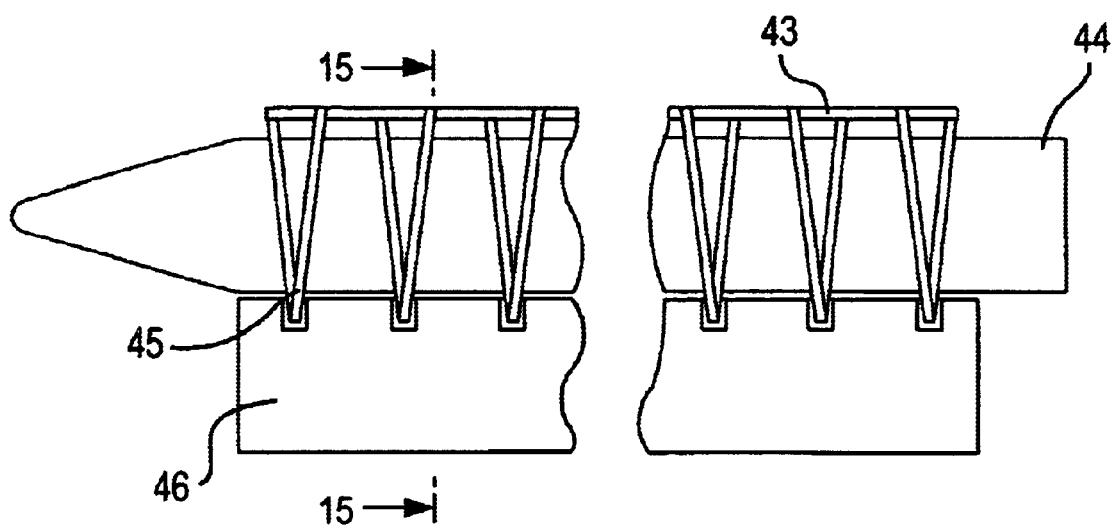
FIG. 14 shows a stent upon the calibration with the free sides of the closed rings oriented in a mandrel.
Figure 15:
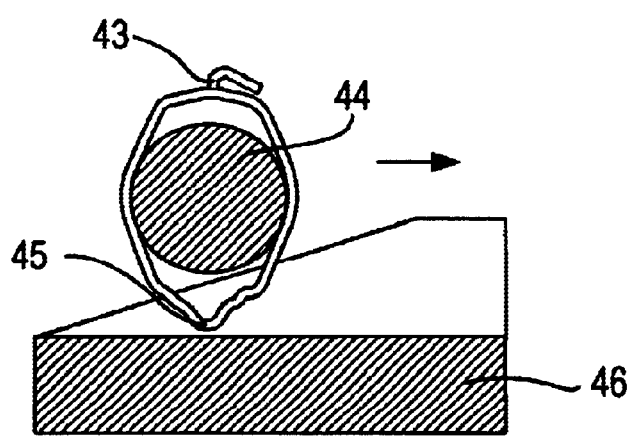
FIG. 15 shows a cross-sectional view of an assembled design across line C—C in FIG. 14.

The technology of the proposed stent design manufacture is described above and generally corresponds to the process of a stent manufacture described in PCT Application No. PCT/IL98/000189, incorporated herein by reference. The only distinction is the necessity of orienting the ring's free sides during the stent calibration or, in other words, orienting of the closed outline short sides. Such an order of the loops short sides disposition can be fulfilled, for example, with the help of a ridged mandrel as is shown in FIGS. 14,15. Upon the calibration by the cylindrical mandrel (44) the stent rings (43) free ends (45) of the closed ring are displaced in a rigid mandrel (46), see FIG. 14. FIG. 15 shows the way how the ridged mandrel (46) with the increasing of the diameter by the cylindrical mandrel (44) gradually shifts into the direction of the arrow up to the acquiring by the stent of a minimal diameter necessary for its deployment and fixation on an uninflated balloon of the conductive catheter. The deployment of an uninflated balloon in a stent lumen should be performed with the help of the ridged mandrel (46) in a position corresponding to that upon the use of the maximal diameter cylindrical mandrel (44). The described manipulation is concluded by the fixation of a stent on the balloon by one of the ways of the generally adopted practice (mechanical tension, partial inflation of the balloon, etc.).

The manufacture of a stent with separate single free loops (37, 38) does not need the use of an additional special equipment (FIGS. 14,15). The manufacturing technology of this stent contains the same steps that are described above.

Thus, from a thin sheet metallic blank a stent of a increased flexibility is produced that does not practically limit the necessary design length, thus securing the properties of transmitting the dynamic impulses from a cardiac muscle to a vessel and practically does not hinder the action on a vessel by a blood flow pulsation. The multitude of relatively free rings are effective also in a vessel longitudinal extent, since they render not simultaneously but individually a massaging action on a vessel during the transmission of impulses from the cardiac muscle. This to a great extent prevents the possibility of restenosis. At the same time with the help of small fragments of the relatively rigid bands in a shape of pockets it is possible somewhat to increase purposefully the rigidity of the stent conditioned sections. By fragmentarily varying the stent flexibility value with the help of separate single free loops, it is possible to achieve by various means the more positive implantation of the stent into the vessels of different anatomic forms, including the cases of the most complicated vessel bifurcations. As a whole the use of the proposed stent permits the stenting procedure to be still more progressive and more purposeful for wide application in clinical practice.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A flexible expandable sheet stent for insertion into the lumen of a vessel of a patient, comprising:

constructive elements forming branches, preliminarily formed in a shape of a stencil on a thin sheet metallic blank surface, which shape comprises one relatively rigid band, consisting of consecutively united pockets, the branches of which form periodically repeating twisting closed outlines having longer and shorter sides, whereas the longer side components of each outline are oppositively located in a shape of a relatively free loop, the shape of which is approaching to a circular shape, forming an independent ring with a fastening point on said relatively rigid band, wherein in said preliminarily formed stencil the constructive elements occupy a primary part of the surface area, excluding that which falls at the stencil openings, radii of formed pockets round-offs and radii of closed free loops short sides round-offs, whereas the width of the openings is executed minimally possible technologically.

2. The flexible expandable sheet stent of claim 1, in which the pockets are formed by a saw-shaped profile bend, a component of the closed free loops outlines, whereas the bend of the pockets is executed into one or alternatively in different sides for an angle of the order of 120°.

3. The flexible expandable sheet stent of claim 1, wherein a polymer loaded thread of a fixed length is located in the consecutively united pockets.

4. The flexible expandable sheet stent of claim 1, wherein the short sides of the closed free loops are fastened by fragments of a relatively rigid band in a shape of the pockets, whereas in case of stent diameter differentiated in its length according to the different diameters and extent of the afflicted vessel by the fragments of the relatively rigid band in a shape of the said pockets the short sides of the closed free loops are fastened in the place of their transition from one stent diameter to the other.

5. The flexible expandable sheet stent of claim 1, which contains single closed free loops, uniformly distributed along the stent length or in places where increased flexibility is most desirable, including a construction variant with one closed free loop, placed in the middle stent part, whereas the other short sides of the loops are executed in a shape of a relatively rigid band consisting of consecutively united pockets.

6. The flexible expandable sheet stent of claim 5, wherein one closed free loop is positioned approximately midway of the stent and the short sides of the other closed free loops comprise a relatively rigid band of the consecutively united pockets.

7. A method of manufacturing a stent, which comprises the steps of:
(a) separating a thin sheet metallic blank with multiple unwasted quantity of the manufactured stents;
(b) executing a calculated geometrical profile stencil of stent constructive elements on the surface of the thin sheet metallic blank;
(c) shaping consecutively united pockets by bending;
(d) deploying the stencil into a step-by-step gauge fixing the distances among the closed free loops;
(e) introducing cylindrical gauges consecutively into all said loops;
(f) positioning appositively the long sides of the each said loop and trying to achieve the stent minimal diameter necessary for an uninflated balloon;
(g) fixation of the stent on an uninflated balloon of the conductive catheter;
(h) installation and fixation of the polymer loaded thread in a passage formed by the chain of the said consecutively united pockets; and
(i) packing of a ready device.

8. The method of claim 7, wherein steps (e) and (f) are not required.

9. A method of manufacturing a stent, which comprises the steps of:
(a) providing a thin sheet metallic blank;
(b) executing a calculated geometric profile stencil of stent constructive elements on the surface of the thin sheet metallic blank;
(c) bending consecutively united pockets to form a line; and;
(d) arranging the stencil onto a rigid substantially cylindrical to form fixed distances among closed free loops.

10. The method of claim 9, which comprises the additional step of after step (c) or (d) of inserting a polymer thread into a passage formed by the chain of consecutively united pockets.

11. The method of claim 10, wherein the polymer thread comprises drugs.

* * * * *